(12) United States Patent
Baker et al.

(10) Patent No.: US 10,279,123 B2
(45) Date of Patent: May 7, 2019

(54) MICROCARTRIDGE

(71) Applicants: Jeff Baker, Orlando, FL (US); Francis Michael Siemer, Orlando, FL (US); Christopher Chung, Orlando, FL (US)

(72) Inventors: Jeff Baker, Orlando, FL (US); Francis Michael Siemer, Orlando, FL (US); Christopher Chung, Orlando, FL (US)

(73) Assignee: Noble International, Inc., Orlando, FL (US)

( * ) Notice: Subject to any disclaimer, the term of this patent is extended or adjusted under 35 U.S.C. 154(b) by 673 days.

(21) Appl. No.: 14/872,674

(22) Filed: Oct. 1, 2015

(65) Prior Publication Data

US 2017/0095619 A1    Apr. 6, 2017

(51) Int. Cl.
*A61M 5/32* (2006.01)
*A61M 5/315* (2006.01)
(Continued)

(52) U.S. Cl.
CPC ...... *A61M 5/3275* (2013.01); *A61M 5/31501* (2013.01); *A61M 5/3202* (2013.01); *A61M 5/3213* (2013.01); *A61M 5/3245* (2013.01); *A61M 5/502* (2013.01); *A61M 5/5086* (2013.01); *A61M 5/31511* (2013.01); *A61M 5/3204* (2013.01); *A61M 5/326* (2013.01);
(Continued)

(58) Field of Classification Search
CPC ............ A61M 5/31501; A61M 5/3202; A61M 5/3213; A61M 5/3243; A61M 5/3245; A61M 5/3275; A61M 5/5013; A61M 5/502; A61M 5/5086; A61M 2005/31508; A61M 2005/3151; A61M 2005/3247; A61M 2005/5033
See application file for complete search history.

(56) References Cited

U.S. PATENT DOCUMENTS

| 4,108,177 A | 8/1978 | Pistor |
| 4,568,336 A | 2/1986 | Cooper |

(Continued)

FOREIGN PATENT DOCUMENTS

WO    WO-03097133 A1 *  11/2003  .......... A61M 5/2033

OTHER PUBLICATIONS

International Search Report and Written Opinion, PCT/US2016/055219; dated Feb. 3, 2017, 18 pages.

*Primary Examiner* — Shefali D Patel

(74) *Attorney, Agent, or Firm* — Timothy H. Van Dyke; Beusse, Wolter, Sanks & Maire PLLC

(57) ABSTRACT

A container for delivering a medicament to a target location includes a housing having a proximal end and a distal end, the housing including a cap locking tab at the distal end, and a vial containing the medicament. The container includes a plunger slidable within the vial from a proximal end to a distal end of the vial to dispel the medicament, an injection member associated with the distal end of the vial, such that the medicament dispelled from the vial passes through the injection member to the target location, and a slidable interaction member associated with the distal end of the vial configured to slide with the vial. An interaction between the slidable interaction member and the cap locking tab causes the cap locking tab to bias outward, and placement of a safety cap on the container after use locks the safety cap onto the container via an interaction with the cap locking tab.

20 Claims, 9 Drawing Sheets

(51) Int. Cl.
   *A61M 5/50*   (2006.01)
   *A61M 5/46*   (2006.01)
   *A61M 5/20*   (2006.01)

(52) U.S. Cl.
   CPC ....... *A61M 5/46* (2013.01); *A61M 2005/2086* (2013.01); *A61M 2005/3151* (2013.01); *A61M 2005/31508* (2013.01); *A61M 2005/3247* (2013.01); *A61M 2005/5033* (2013.01); *A61M 2205/583* (2013.01); *A61M 2205/59* (2013.01)

(56) References Cited

U.S. PATENT DOCUMENTS

| | | | |
|---|---|---|---|
| 4,643,200 A | 2/1987 | Jennings, Jr. | |
| 4,695,274 A | 9/1987 | Fox | |
| 5,147,303 A | 9/1992 | Martin | |
| 5,578,014 A | 11/1996 | Erez et al. | |
| 5,873,856 A | 2/1999 | Hjertman et al. | |
| 6,203,529 B1 | 3/2001 | Gabriel et al. | |
| 6,537,257 B1 | 3/2003 | Wien | |
| 6,926,697 B2 | 8/2005 | Malenchek | |
| 6,997,906 B2 | 2/2006 | Langley et al. | |
| 7,837,657 B2 | 11/2010 | Mazidji et al. | |
| 2004/0193110 A1 | 9/2004 | Giambattista et al. | |
| 2004/0236284 A1* | 11/2004 | Hoste ............... | A61M 5/326 604/198 |
| 2005/0171477 A1 | 8/2005 | Rubin et al. | |
| 2007/0265568 A1 | 11/2007 | Tsals et al. | |
| 2009/0312703 A1* | 12/2009 | Pickhard .............. | A61M 5/322 604/110 |
| 2011/0319864 A1 | 12/2011 | Beller et al. | |
| 2013/0274677 A1 | 10/2013 | Ekman et al. | |
| 2013/0317480 A1* | 11/2013 | Reber ................ | A61M 5/2033 604/506 |

* cited by examiner

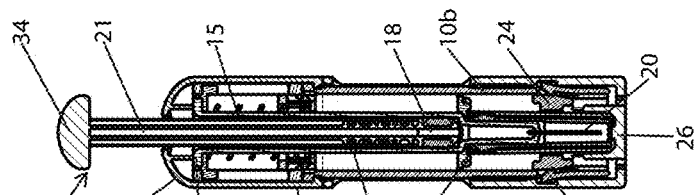
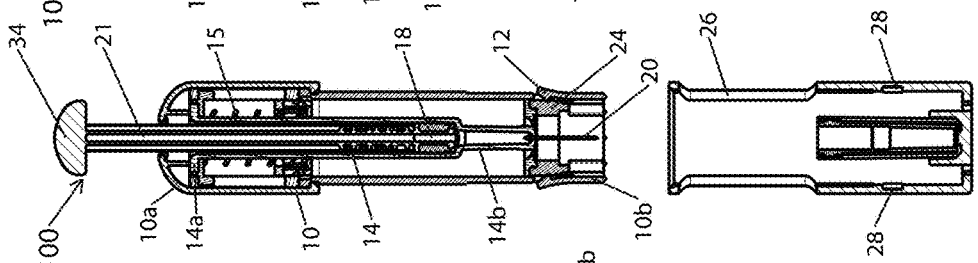
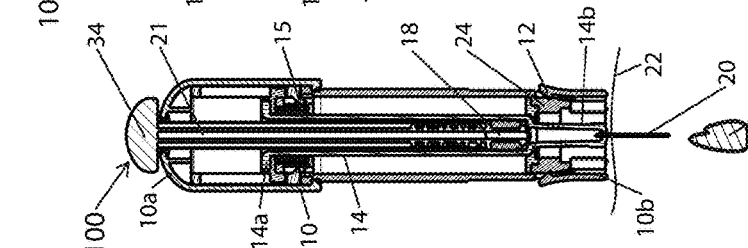
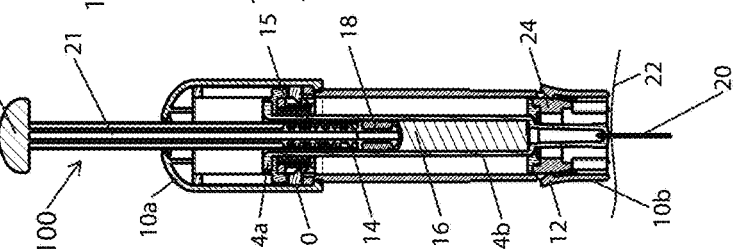
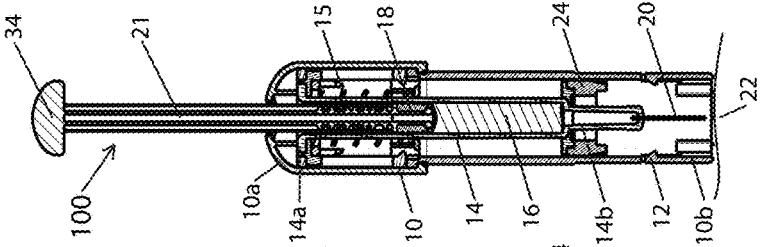
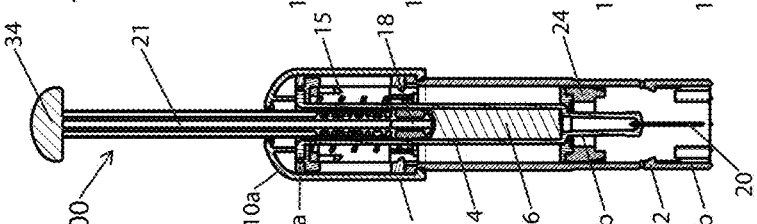
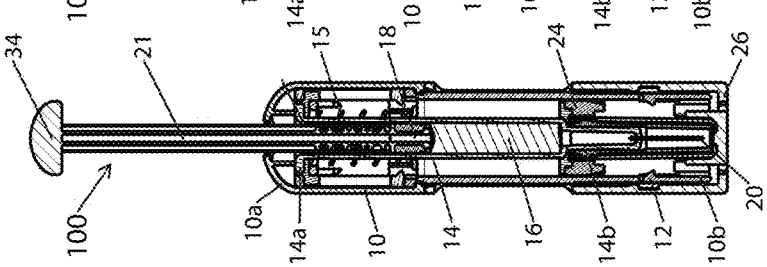
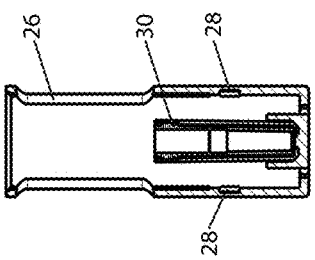

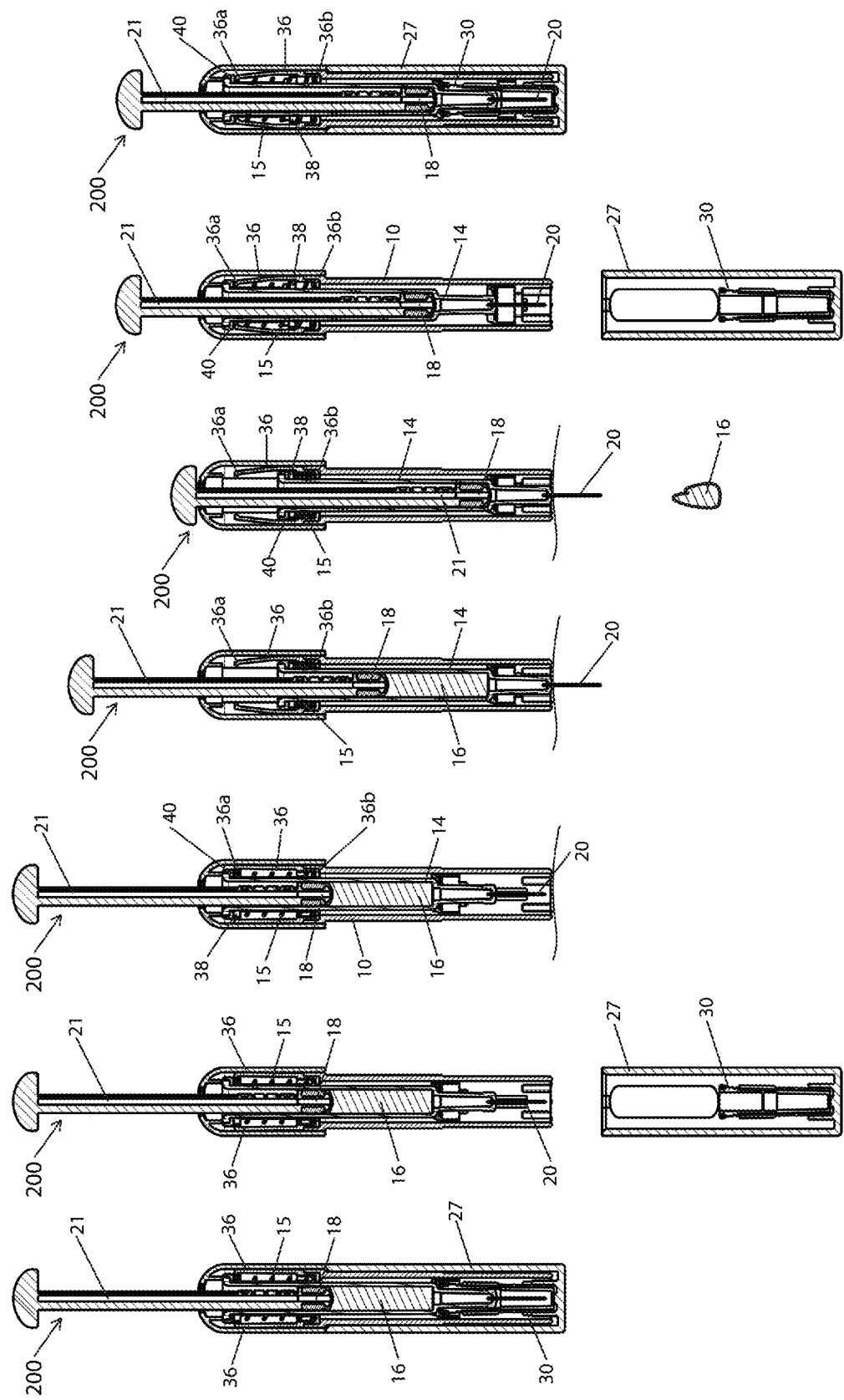

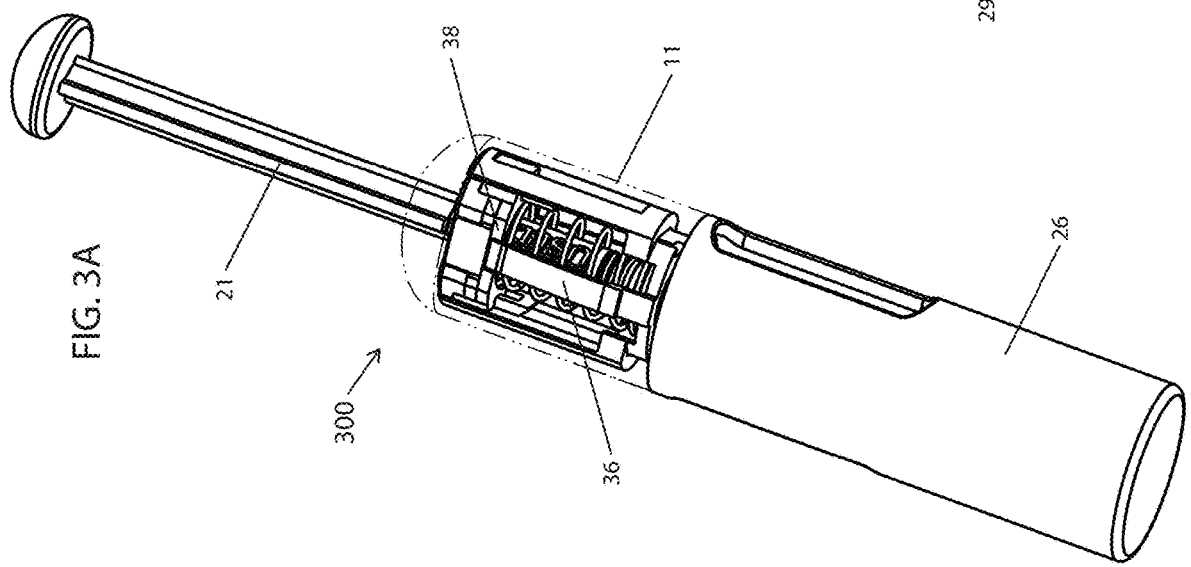
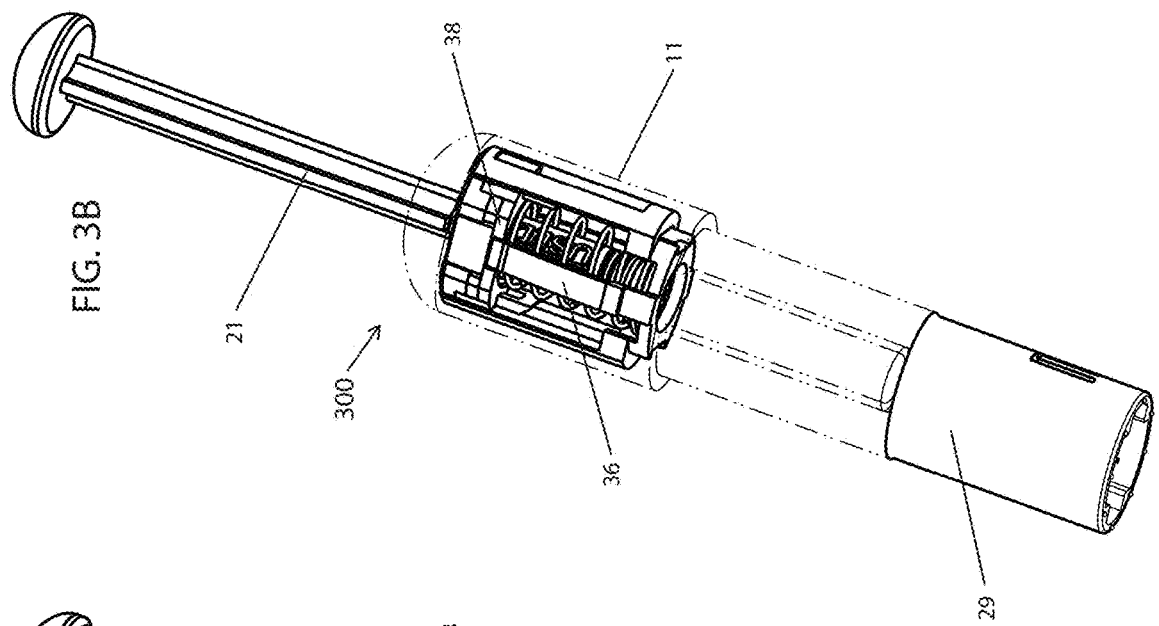

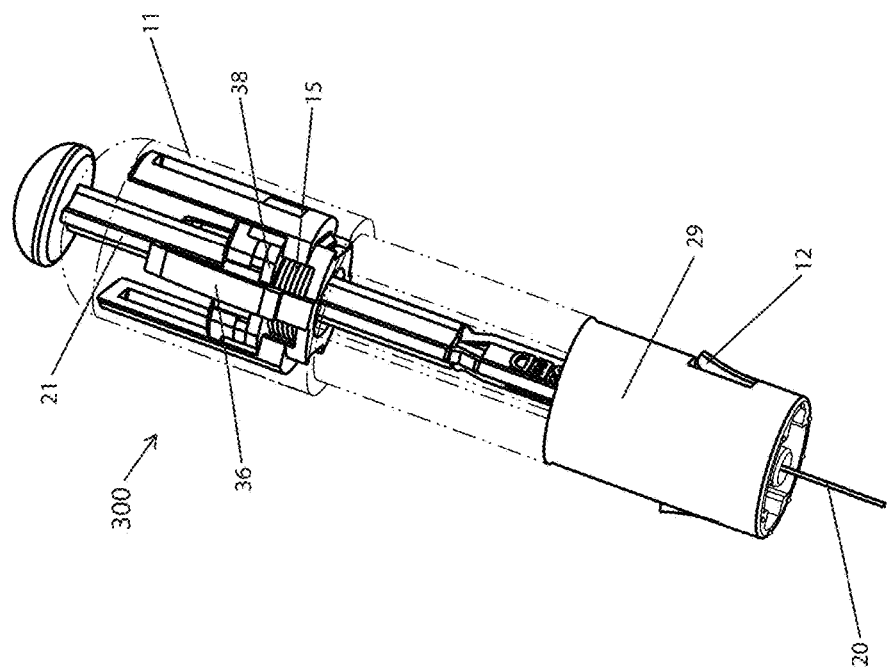
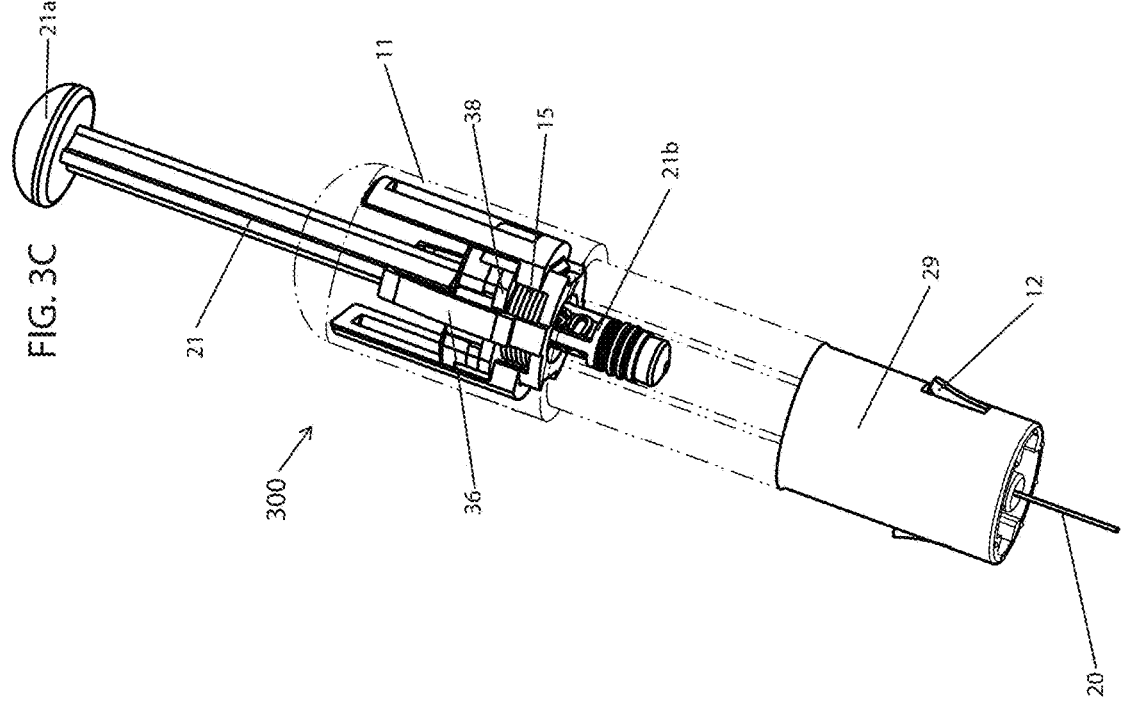

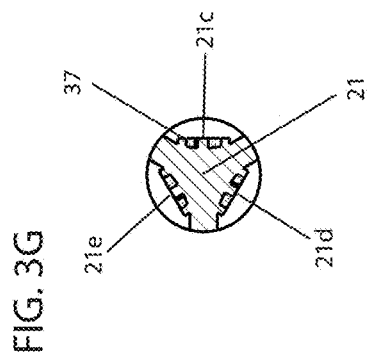
FIG. 3G
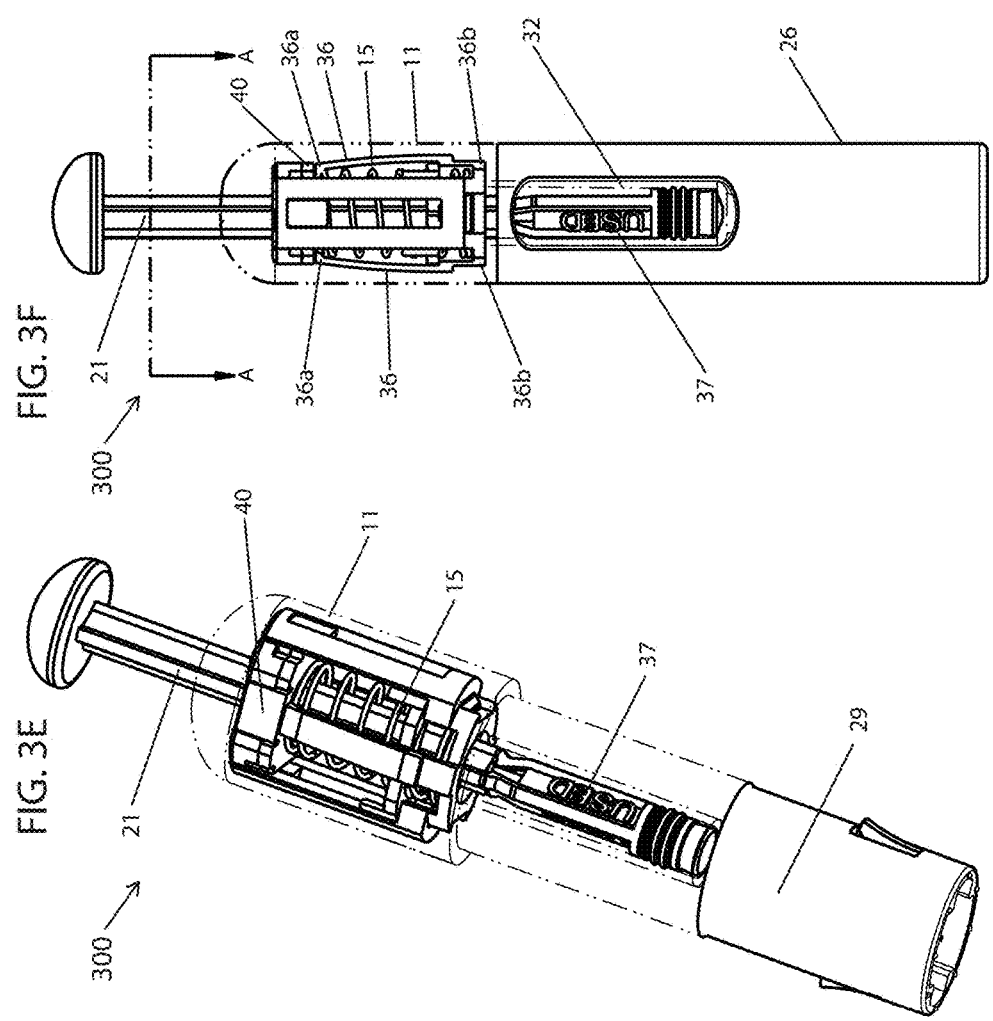
FIG. 3F
FIG. 3E

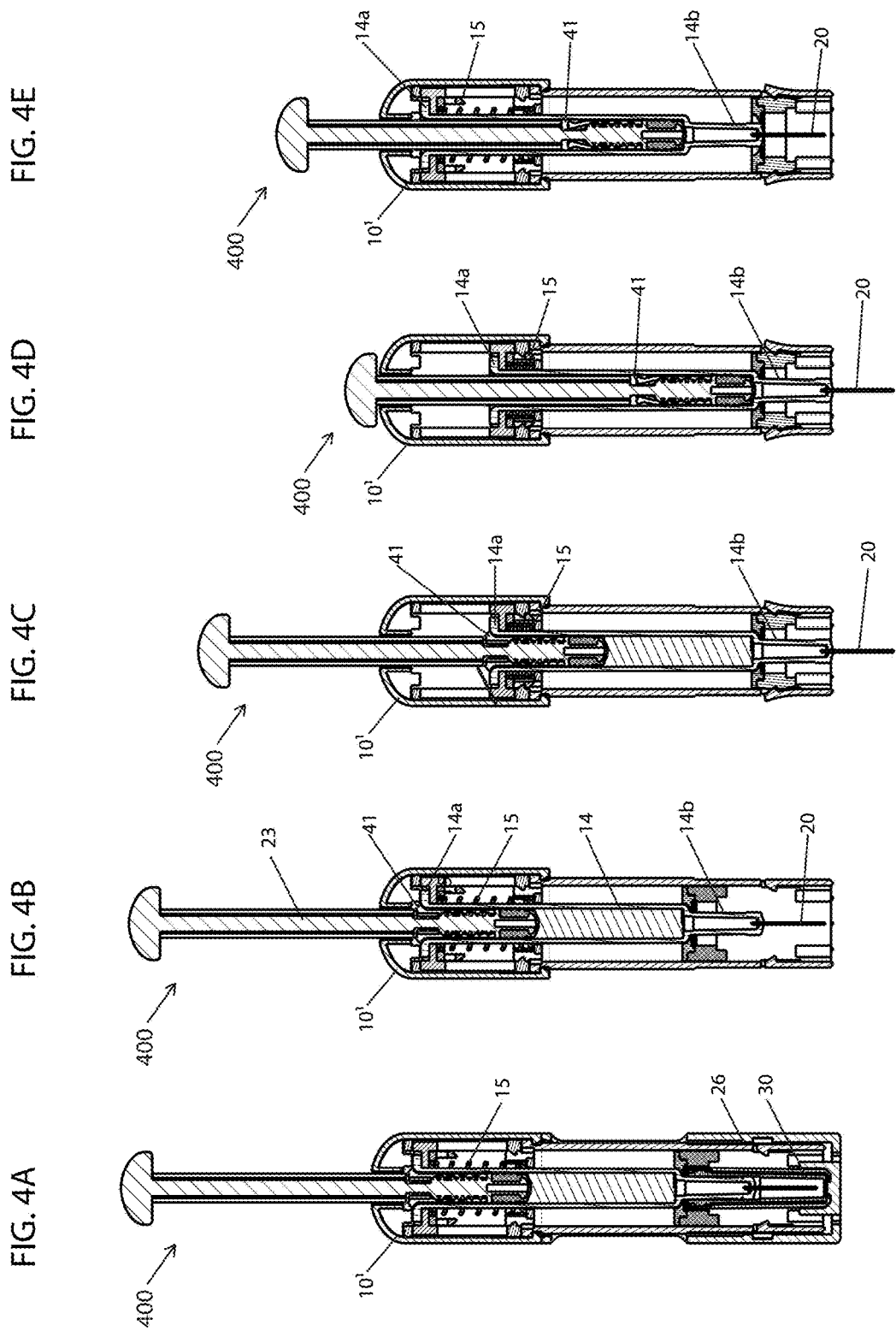

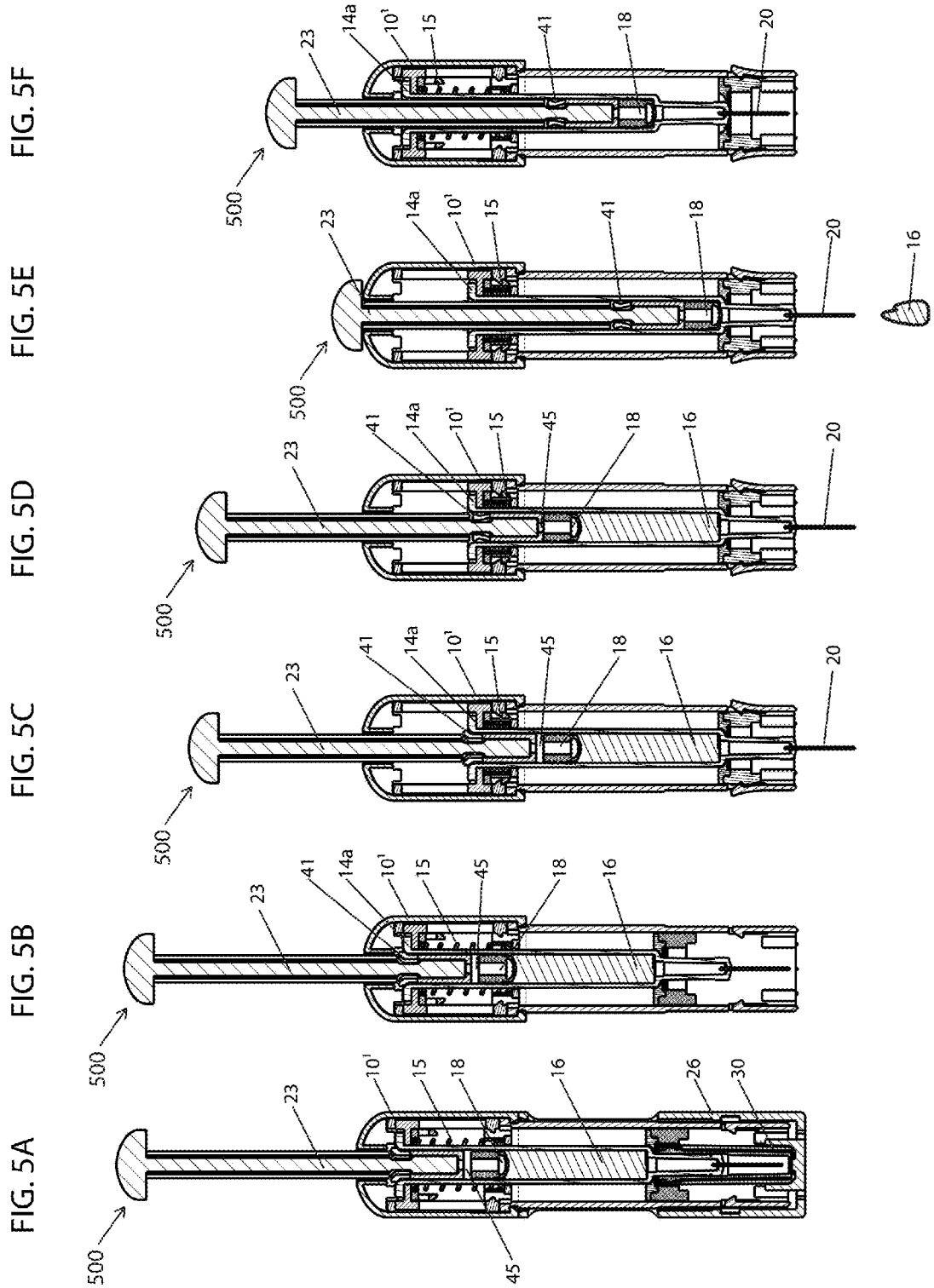

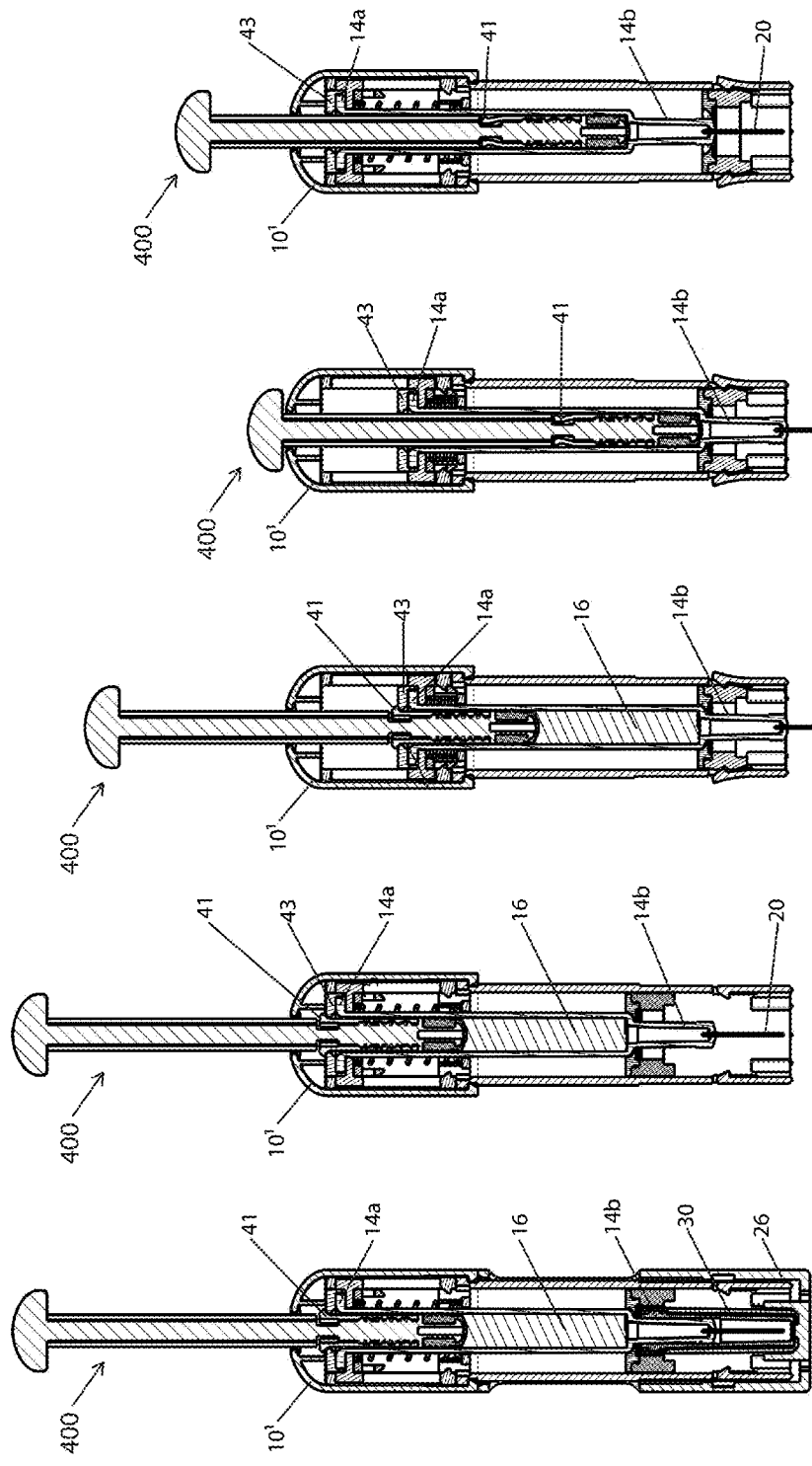

MICROCARTRIDGE

BACKGROUND

Injection devices are used for administering medications via a needle. Certain disease states require those suffering from them to receive injections often. Those suffering from diabetes, for example, require frequent administration of injections, which are typically self-administered often in a non-clinical setting. Injection devices including auto-injectors or prefilled syringe injection devices are typically used to self-administer injections and most of these devices are single-use injection devices in order to minimize the risk of infections associated with re-use of the injection device by the same or a different user. Reducing accidental needle stick injuries caused by contaminated needles is also a concern. Therefore, a need exists for the prevention of re-using needles and/or injection devices, as well as prevention of accidental needle-sticks by users of injection devices.

SUMMARY

In one embodiment, a container for delivering a medicament to a target location is provided. The container including a housing having a proximal end and a distal end, the housing including a cap locking tab at the distal end, the container further including a vial having a proximal end and a distal end, the vial configured to contain a medicament, the vial being movable relative to the housing. The container further includes a plunger associated with the proximal end of the vial, the plunger configured to slide within the vial from the proximal end to the distal end of the vial to dispel the medicament from the vial. The plunger may be associated with a plunger rod configured to interact with the plunger. The container may further include an injection member associated with the distal end of the vial, such that medicament dispelled from the vial passes through the injection member to the target location. A slidable interaction member is associated with the distal end of the vial, the slidable interaction member configured to slide with the vial; and a safety cap including a cap groove, the safety cap configured to interact with the distal end of the housing. Moving the vial toward the distal end of the housing causes the slidable interaction member to interact with the cap locking tab, biasing the cap locking tab outward, such that adjoining the safety cap to the distal end of the housing causes the cap groove to interact with the cap locking tab, preventing removal of the safety cap after use of the container.

In another embodiment, a container for delivering a medicament to a target location is provided including a housing having a proximal end and a distal end, a vial including a proximal end and a distal end, the vial configured to contain a medicament, the vial configured to move relative to the housing, a plunger slidable within the vial and a plunger rod associated with the plunger, the plunger configured to slide within the vial from the proximal end to the distal end of the vial to deliver the medicament, and a plunger locking member in the proximal end of the housing, the plunger locking member including a proximal end and a distal end, wherein the proximal end of the plunger locking member is biased toward a periphery of the housing prior to actuation of the plunger and/or plunger rod, and the proximal end of the plunger locking member is biased toward the plunger rod following actuation of the plunger and/or plunger rod. The container may further include a slidable plunger lock release member disposed between the vial and the proximal end of the plunger locking member and associated with the slidable plunger locking unit prior to actuation of the plunger and/or plunger rod, biasing the plunger locking member toward the periphery, wherein following actuation of the plunger, the slidable plunger locking unit slides toward the distal end of the device, sliding the plunger lock release member toward the distal end, such that the proximal end of the plunger locking member is biased toward the plunger rod, following delivery of medicament, the vial moves toward the proximal end of the device, the injection member is retracted within the housing, and the slidable plunger locking unit moves to the distal end to abut the proximal end of the plunger locking member preventing a subsequent actuation of the plunger and/or plunger rod.

In a further embodiment, a method of injecting medicament into a subject is provided. The method includes obtaining a container for delivering a medicament to a target location. The method further includes applying the distal end of the container to a target area on the subject and depressing the plunger rod to insert the injection member and deliver the medicament. In a further embodiment, the method may include releasing the plunger rod to allow retraction of the injection member, wherein upon retraction, the injection member is locked within the housing. In still a further embodiment, the method may include removing the safety cap prior to the applying step. In yet a further embodiment, the method may include attaching the safety cap subsequent to the releasing step, whereby the safety cap is permanently locked.

BRIEF DESCRIPTION OF THE DRAWINGS

FIG. 1A is a cross-sectional view of an embodiment of a container for delivering a medicament to a target location prior to use, having a safety cap on a distal end thereof.

FIG. 1B is a cross sectional view of the container embodiment of FIG. 1A following removal of the safety cap, prior to activation of the container.

FIG. 1C is a cross sectional view of the container embodiment of FIG. 1B upon placement against a target surface at the target location.

FIG. 1D is a cross sectional view of the container embodiment of FIG. 1C following partial activation.

FIG. 1E is a cross sectional view of the container embodiment of FIG. 1D following complete activation.

FIG. 1F is a cross sectional view of the embodiment of FIG. 1E following retraction of the injection member from the target surface.

FIG. 1G is a cross sectional view of the embodiment of FIG. 1F following replacement and locking of the safety cap onto the container.

FIG. 2A is a cross sectional view of another embodiment of a container for delivering a medicament to a target location with a safety cap on the distal end of the container.

FIG. 2B is a cross sectional view of the embodiment of FIG. 2A, following removal of the safety cap.

FIG. 2C is a cross sectional view of FIG. 2B upon placement against the skin.

FIG. 2D is a cross sectional view of the container of FIG. 2C following activation of the container.

FIG. 2E is a cross sectional view of the container of FIG. 2D following delivery of the medicament.

FIG. 2F is a cross sectional view of the container of FIG. 2E following use of the container and retraction of the injection member.

FIG. 2G is a cross sectional view of the container of FIG. 2F following replacement of the safety cap over the end of the container.

FIG. 3A is a perspective view of an embodiment of a container prior to removal of the safety cap before use.

FIG. 3B is a perspective view of the embodiment of the container of FIG. 3A following removal of the safety cap before use.

FIG. 3C is a perspective view of the embodiment of the container of FIG. 3B following actuation of the container causing deliver of the injection member.

FIG. 3D is a perspective view of the embodiment of the container of FIG. 3C following deliver of the medicament from the container.

FIG. 3E is a perspective view of the embodiment of the container of FIG. 3F following retraction of the injection member.

FIG. 3F is a perspective view of the embodiment of the container of FIG. 3E following retraction of the injection member and replacement of the safety cap in a locked position.

FIG. 3G is a cross sectional view of an embodiment of the plunger rod taken at line A-A of FIG. 3F.

FIG. 4A is a is a cross sectional view of another embodiment of a container for delivering a medicament to a target location with a safety cap on.

FIG. 4B is a cross sectional view of the embodiment of FIG. 4A, following removal of the safety cap.

FIG. 4C is a cross sectional view of FIG. 4B following activation of the container by actuation of the plunger and delivery of the injection member.

FIG. 4D is a cross sectional view of the container of FIG. 4C following deliver of medicament from the container.

FIG. 4E is a cross sectional view of the container of FIG. 2D following retraction of the injection member.

FIG. 5A is a cross sectional view of a further embodiment of a container for delivering a medicament to a target location with a safety cap on the distal end of the container.

FIG. 5B is a cross sectional view of the embodiment of FIG. 5A, following removal of the safety cap.

FIG. 5C is a cross sectional view of FIG. 5B following application of a force on the plunger rod, and delivery of the injection member.

FIG. 5D is a cross sectional view of the container of FIG. 5C following biasing inward of the flexible tabs on the plunger rod.

FIG. 5E is a cross sectional view of the container of FIG. 5D following delivery of the medicament.

FIG. 5F is a cross sectional view of the container of FIG. 5E following use of the container and retraction of the injection member.

FIG. 6A is a cross sectional view of a further embodiment of a container for delivering a medicament to a target location with a safety cap on the distal end of the container.

FIG. 6B is a cross sectional view of the embodiment of FIG. 6A, following removal of the safety cap.

FIG. 6C is a cross sectional view of FIG. 6B following application of a force on the plunger rod, movement of the vial, and delivery of the injection member.

FIG. 6D is a cross sectional view of the container of FIG. 6C following biasing inward of the flexible tabs on the plunger rod and delivery of medicament.

FIG. 6E is a cross sectional view of the container of FIG. 6D following use of the container and retraction of the injection member.

DETAILED DESCRIPTION

Figure 7:
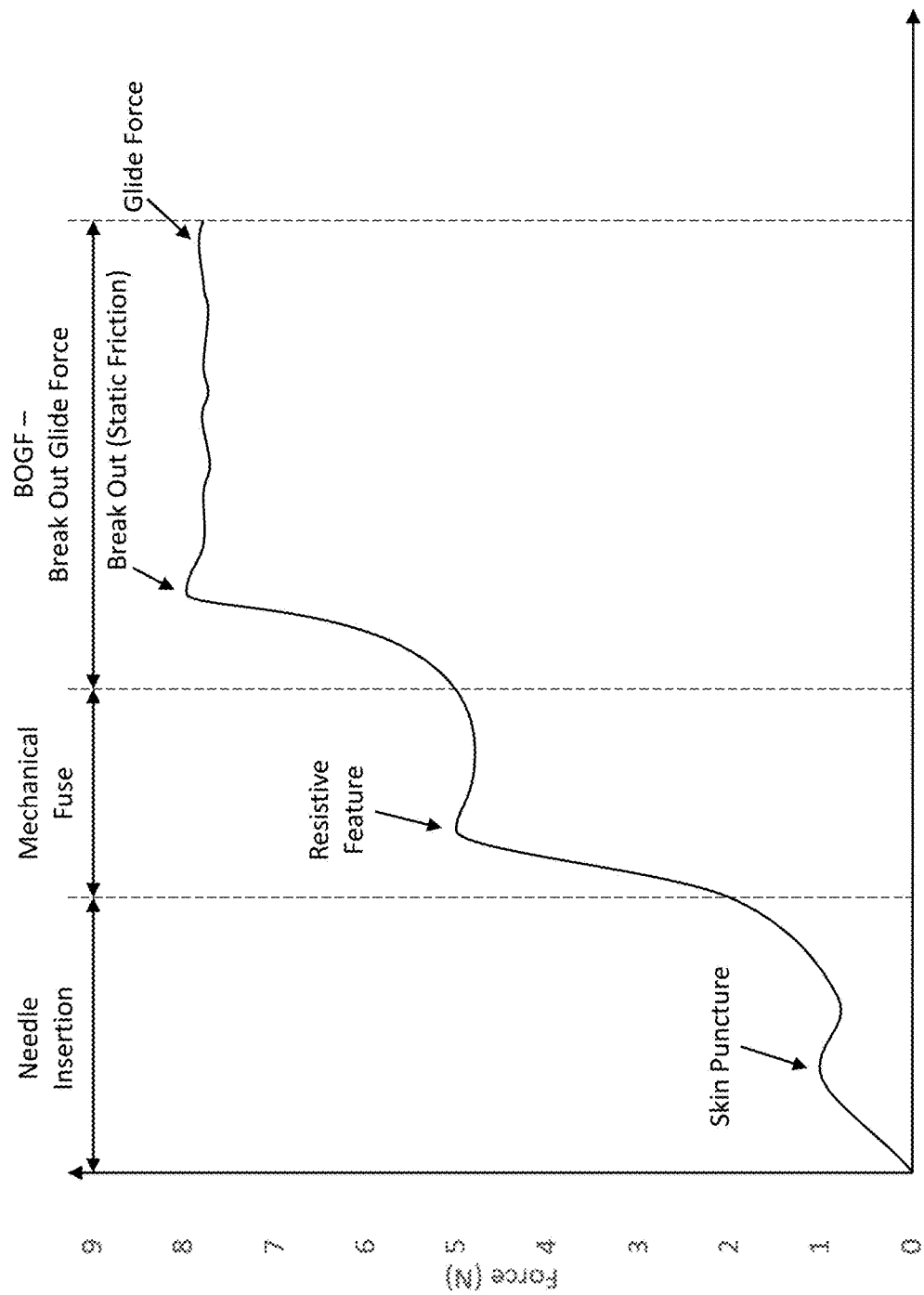
FIG. 7 includes a graphical illustration of the various forces encountered during use of the container embodiments described herein.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another. The modifier "about" used in connection with a quantity is inclusive of the stated value and has the meaning dictated by the context. It is to be noted that all ranges disclosed within this specification are inclusive and are independently combinable.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7. As another non-limiting example, a range of "between 20 and 10" can also include the values 20, 10.

The term "adjacent" as used herein, includes but is not limited to near, associated with, or in close proximity to.

The term "threshold resistance force" as used herein, includes but is not limited to a force required to initiate movement of a plunger rod relative to a vial. In an embodiment, it is the force at which the flexible tabs releieve to initiate movement of the plunger rod relative to the vial. The "threshold" may be adjustable based on variables including, but not limited to, type of medicament, amount of force required of the biasing member, contact and interactivity between various components of the container including friction between the plunger and the inner surface of the vial, and relative movement there between, and other variables known to those skilled in the art.

The inventors herein have identified a need for an injection device with features for safety both before and after use as well as additional features for ease of use of the device.

In one embodiment, a container 100 for delivering a medicament to a target location is provided in the stepwise cross sectional views shown in FIGS. 1A-1G. The container 100 includes a housing 10 having a proximal end 10*a* and a distal end 10*b*, the housing 10 including a cap locking tab 12 near the distal end 10*b*, the container 100 further including a vial 14 having a proximal end 14*a* and a distal end 14*b*, the vial 14 configured to contain a medicament 16, the vial 14 being movable relative to the housing 10, and a biasing member 15 disposed between the vial 14 and the housing 10. Prior to use of the container 100, a safety cap 26 disposed over the distal end of the housing 10*b* must be removed as shown in FIGS. 1A-1B. The container 100 further includes a plunger 18 slidable within the vial and a plunger rod 21 associated with the plunger 18. The plunger 18 is configured to slide within the vial 14, from the proximal end 14*a* to the distal end 14*b* of the vial 14, to dispel the medicament 16 from the vial 14. An injection member 20 is associated with the distal end of the vial 14*b*, such that medicament 18 dispelled from the vial 14 passes through the injection member 20 to the target surface 22 or target location. The target surface or location may include a target area on a user, such as, but not limited to an area of skin indicated for an injection.

A slidable interaction member 24 is associated with the distal end of the vial 14*b*, the slidable interaction member 24 configured to slide with the vial 14; and a safety cap 26 including a cap groove 28, the safety cap 26 configured to interact with the distal end of the housing 10*b*. Actuation of the plunger 18 by moving the plunger 18 toward the distal end of the housing 10*b* moves the vial 14 toward the distal end of the housing 10*b*, (in embodiments where a plunger rod 21 is associated with the plunger 18, as in FIGS. 1A-1G, this can be done by actuating the plunger rod 21, which in turn, actuates the plunger 18). This biases the biasing member 15, and causes the injection member 20 to traverse the target surface 22. Moving the vial 14 toward the distal end of the housing 10 causes the slidable interaction member 24 to interact with the cap locking tab 12, biasing the cap locking tab 12 outward, such that later adjoining the safety cap 26 to the distal end of the housing 10 causes the cap groove 28 of the safety cap 26 to interact with the cap locking tab 12, thereby preventing removal of the safety cap 26 after use of the container 100, see FIG. 1D, FIG. 1G.

Further movement of the plunger 18 toward the distal end of the housing 10*b* causes the plunger 18 to slide relative to the vial 14 toward the distal end 14*b*, such that medicament 16 within the vial 14 is delivered through the injection member 20 as shown in FIG. 1E. Release of the pressure against the plunger 18 and/or the plunger rod 21 causes release of the biasing member 15 as shown in FIG. 1F, so as to retract the injection member 20 into the housing 10 as the vial 14 moves toward the proximal end of the housing 10. Adjoining the safety cap 26 onto the distal end of the housing 10*b* causes the cap groove 28 to interact with the cap locking tab 12, as shown in FIG. 1G, wherein the safety cap is in a locked position, preventing removal of the safety cap after use of the container 100.

The safety cap 26 may further include an injection member cover 30 there within as shown in FIGS. 1A, 1B, 1F, and 1G, configured to surround the injection member 20 when the safety cap 26 is adjoined to the distal end 10*b* of the housing 10. The safety cap 26 and/or the injection member cover 30 may be provided to maintain sterility of the injection member 20 prior to use of the container 100, and to provide protection from accidental needle sticks to a user via the injection member 20 prior to and following injection.

In some, non-limiting embodiments, at least a portion of the housing may include a viewing window 32 providing a view into the housing 10 (shown in FIGS. 3A-3F).

In a further non-limiting embodiment, the plunger rod 21 may include a plunger contact member 34 at the proximal plunger rod end 21*a* as shown in FIGS. 1A-1G. The plunger contact member 34 may include a material to enhance the gripping contact between the user and the plunger contact member 34 and prevent slipping during use. The material may include a rubber material in one non-limiting embodiment. Other similar materials known to those skilled in the art may be used to prevent slipping. Further, an etched or other irregular surface may be included on the plunger contact member 34 in place of, or in addition to the rubber material, to increase and maintain contact between the user and the plunger contact member 34 during use of the container 100. In non-limiting embodiments, the rubber material provides a more secure grip to a user; the shape and size of the plunger contact member can vary to provide a flatter portion for better grip, or another user friendly shape to enhance the injection experience and reduce slipping off of the plunger contact member during use.

A pictorial instruction for use (IFU) may be provided in non-limiting embodiments of the container 100 described herein. In one non-limiting embodiment, the pictorial IFU may include text, pictures, or other indicators and may be located on any portion of the container 100. There may be one or more pictorial IFU's and the pictorial IFU may include audio in place of or in addition to visual pictorial IFU indicators, in non-limiting embodiments. In one non-limiting example, a pictorial IFU may include a series of light emission diodes (LEDs) on the plunger body in the shape of an arrow pointing downward indicating to a user to press the plunger toward the distal end of the housing 10*b* in a first step, another pictorial IFU such as a series of LED's in the shape and color of a octagon to signal stop or wait to the user, to indicate that the injection is in process, and the medicament 16 is slowly being delivered to the target area, and not to remove the container 100 from the target surface 22. Upon completion of medicament delivery to the target area, an upright green arrow shown in LEDs may be provided on the housing 10, for example, indicating that removal of the container 100 from the target surface 22 is suggested. As aforementioned, the pictorial IFU may not be limited to the embodiments described herein. An LCD showing photos or video demonstrating, for example, use of the device may also be provided as a pictorial IFU. In other non-limiting embodiments, a combination of lights and sound may be used to guide a user by way of the pictorial IFU, for example. The location and type of pictorial IFU described herein are provided for example only, and are not intended to be limiting.

In another non-limiting embodiment shown in the cross sectional embodiments of FIGS. 2A-2G the container 200 for delivering a medicament to a target location may further include a plunger locking member 36 in the proximal end of the housing 10. The plunger locking member 36 including a proximal end 36*a* and a distal end 36*b*, wherein the proximal end 36*a* of the plunger locking member is biased toward the housing 10 prior to actuation of the plunger 18 (see FIGS. 2A-2C) and the proximal end 36*a* of the plunger locking member is biased toward the plunger 18 following actuation of the plunger 18 (via the plunger rod 21 in non-limiting embodiments) as shown in FIGS. 2D-2G. The container may further include a slidable plunger lock release member 38 disposed between the vial 14 and the proximal end of the plunger locking member 36*a* and associated with a slidable plunger locking unit 40 prior to actuation of the plunger 18 or plunger rod 21, biasing the plunger locking member proximal end 36a toward the housing 10 and away from the plunger rod 21. Following actuation of the plunger 18 or plunger rod 21, the slidable plunger locking unit 40 slides toward the distal end of the housing 10, sliding the plunger lock release member 38 toward the distal end, such that the proximal end of the plunger locking member 36a is biased toward the plunger rod 21. During actuation of the container, wherein the vial 14 moves toward the distal end of the housing, a biasing member 15 is biased as shown in FIGS. 2D, 2E. Following delivery of medicament 16, the biasing member 15 is extended as shown in FIG. 2F once the plunger rod 21 is released, and the vial 14 moves toward the proximal end of the housing 10 as shown in FIG. 2F. Consequently, the injection member 20 is retracted, and the slidable plunger locking unit 40 moves to the proximal end of the housing 10 as shown in FIGS. 2F and 2G to abut the proximal end of the plunger locking member 36a as shown in FIGS. 2F-2G, preventing a subsequent actuation of the plunger 18 or the plunger rod 21.

Preventing the plunger lock release member 38 from moving to its pre-actuation location in the proximal end of the housing 10 disposed between the plunger locking member proximal end 36a and the vial 14 maintains the plunger rod 21 in a locked position as shown in FIG. 2F-2G, wherein the slidable plunger locking unit 40 has returned to its pre-actuation position and abuts the plunger locking member 36 keeping the plunger rod 21 in a locked position and preventing actuation of the plunger rod 21. This embodiment prevents, in one example, accidental needle-sticks by maintaining the injection member 20 in a safe, protected, retracted position within the housing 10 following use of the container 100, and furthermore, prevents subsequent use of the container 100 following an initial use.

A safety cap 27 may be placed over the distal end of the housing 10 before use of the container (as shown in FIG. 2A), and removed from the distal end by a user before use of the container as shown in FIG. 2B. Once the container 100 has been used, and the injection member 20 has been retracted as shown in FIG. 2F, the safety cap 27 may be placed over the distal end of the housing 10 to further protect users from accidental injection member 20 exposure. The safety cap 27 may include an injection member cover 30 as shown.

FIGS. 3A-3E include perspective views of another embodiment of a container 300 and FIG. 3F includes a side view of the embodiment 300, demonstrating non-limiting sequential steps of use of the container 300. In the non-limiting embodiment 300, the safety cap 26 is shown in FIG. 3A. The embodiment 300 includes both the safety cap 26 having the cap groove 28 to interact with a cap locking tab 12 on the housing 11. The cap locking tab 12 interacts with the slidable interaction member 24 as described above in reference to FIGS. 1A-G following activation of the container 300 (slidable interaction member not visible in FIGS. 3A-E).

The embodiment 300 of FIGS. 3A-3F further includes a plunger locking member 36 in the proximal end of the housing 11. The plunger locking member 36 including a proximal end 36a and a distal end 36b, wherein the proximal end 36a of the plunger locking member 36 is biased toward the housing 11 prior to actuation of the plunger 18 and/or plunger rod 21 (see FIGS. 3A-3C) and the proximal end 36a of the plunger locking member is biased toward the plunger rod 21 following actuation of the plunger 18 (via the plunger rod 21 in non-limiting embodiments) as shown in FIGS. 3D-3F. The container 11 may further include a slidable plunger lock release member 38 disposed between the vial 14 and the proximal end of the plunger locking member 36a and associated with a slidable plunger locking unit 40 prior to actuation of the plunger 18 or plunger rod 21, biasing the plunger locking member proximal end 36a toward the housing 11 and away from the plunger rod 21. Following actuation of the plunger 18 or plunger rod 21, the slidable plunger locking unit 40 (shown in this non-limiting embodiment in association with the vial 14) slides toward the distal end of the housing 11, sliding the plunger lock release member 38 toward the distal end, such that the proximal end of the plunger locking member 36a is biased toward the plunger rod 21. During actuation of the container 300, wherein the vial 14 moves toward the distal end of the housing, a biasing member 15 is biased as shown in FIGS. 3C-3D. Following delivery of medicament 16, the biasing member 15 is extended as shown in FIG. 3E-3F once the plunger rod 21 is released, and the vial 14 moves toward the proximal end of the housing 11, and the injection member 20 is retracted into the housing 11 as shown in FIGS. 3E-3F. The slidable plunger locking unit 40 moves to the proximal end of the housing 11 along with the proximal portion of the vial 14 as shown in FIGS. 3E-3F to abut the proximal end of the plunger locking member 36a as shown in FIGS. 3E-3F, preventing a subsequent actuation of the plunger 18 or the plunger rod 21 resulting from the contact between the slidable plunger locking unit 40 and the plunger locking member proximal end 36a. As provided in FIG. 3F, following use of the container 300, the safety cap 26 may be placed over the distal end of the housing 11, and the cap groove 28 may interact with the cap locking tab 12 to prevent removal of the safety cap 26 from the housing 11.

In this non-limiting embodiment, a visual indicator 37 may be provided, as shown, on one or more of the first surface 21c, second surface 21b or third surface 21d of the plunger rod 21 triangular body as shown in FIGS. 3A-G. The visual indicator 37 may provide a status of use to the user of the container 300. For example, prior to use, the visual indicator 37 may not be shown (i.e., it may be hidden under another component of the container 300, or a portion of the housing that is non-transparent, i.e., opaque in a non-limiting example) and following use or during use of the container 300 (i.e., after actuation of the plunger 18), the visual indicator may be shown, in a non-limiting embodiment. In one embodiment, as shown in FIGS. 3A-3F, the visual indicator 37 may include the word USED, such that it can be used to communicate to a user that the container 300 has been used, and in this embodiment, the USED visual indicator 37 may only be readable once an injection with the container has completed. Therefore, the visual indicator 37 may appear within a viewing window 32 of the container such that a user may view the visual indicator 37 only after having used the container as shown in FIG. 3E-3F. This feature is beneficial in preventing multiple uses of a used device and/or preventing unwanted needle-sticks with a used device.

In a non-limiting embodiment, the housing may include a non-transparent portion to prevent a user from viewing the injection member during use of the container. The term "non-transparent" as used herein includes, but is not limited to, opaque, translucent, and may include at least a portion of the housing having one or more of these features which may occur by use of a material encompassing these features, or with a finish on the container, a surface treatment, a paint, and also further includes a label which may prevent a user from viewing the injection member during the course of using the container.

FIGS. 3B-3E show a non-transparent region 29 of the housing adjacent to the injection member, wherein the non-transparent region 29 prevents a view of the injection member 20 by the user during use of the container 300 to decrease user-anxiety associated with the handling of injection members 20, i.e., needles.

In a further embodiment, the plunger rod 21 includes a proximal plunger rod end 21a and a distal plunger rod end 21b (as shown in FIG. 3C), wherein the plunger rod comprises a triangular body comprising a first surface 21c, a second surface 21d and a third surface 21e, in one non-limiting embodiment shown in FIG. 3G. The visual indicator 37 may be visible from any angle by the user due to the triangular shaped body of the plunger rod 21. FIG. 3G provides a cross-sectional view of the plunger rod 21 taken at line A-A in FIG. 3F.

FIGS. 4A-E provide sequential cross-sectional views of a container embodiment 400 for delivering a medicament to a target location, including a housing 10' having a proximal end and a distal end, a vial 14 having a proximal end 14a and a distal end 14b, the vial 14 configured to contain a medicament in some non-limiting embodiments. The vial 14 configured to move relative to the housing 10'. An injection member 20 associated with the distal end of the vial 14b, such that medicament delivered from the vial 14 passes through the injection member 20 to the target location. The container embodiment 400 further includes a plunger 18 slidable within the vial 14 from the proximal end to the distal end of the vial 14 to dispel the medicament from the vial 14 or to simulate movement of a plunger 18 in a medicament delivery device, in an alternative embodiment. A plunger rod 23 having a proximal end and a distal end, the distal end of the plunger rod associated with the plunger, said plunger rod 23 being slidable relative to the vial 14. Application of a force to the plunger rod causes the vial 14 to move toward the distal end of the housing delivering the injection member 20, upon reaching a threshold resistance force wherein at least one resistance feature associated with the plunger rod 23 allows the plunger rod 23 to slide within the vial 14 toward the distal end of the vial to deliver the medicament.

In one, non-limiting embodiment shown in FIGS. 4A-4E, the at least one resistance feature may include at least one flexible tab 41 associated with a portion of the plunger rod 23, configured to interact with the proximal end of the vial 14. The plunger rod 23 and plunger 18 are shown as connected or one continuous component, in the embodiment shown in FIGS. 4A-E, and in some alternative embodiments, these components may be separate and distinct from one another as can be seen in FIG. 5, wherein prior to actuation of the plunger rod 23, a space is disposed between the two components.

In FIGS. 4A-C movement of the plunger rod 23 toward the distal end of the housing 10' causes the at least one flexible tab 41 to press against the vial 14, a biasing member 15 disposed within the housing is compressed as seen in FIG. 4C, and the vial 14 to move toward the distal end of the housing 10' delivering the injection member 20 as shown in FIG. 4C. Further movement of the plunger rod 23 toward the distal end of the housing 10' as shown in FIG. 4D, causes the at least one flexible tab 41 to flex inward toward the plunger rod 23, and the plunger rod 23 to slide further within the vial 14 toward the distal end of the vial 14 to deliver medicament there within. Following deliver of medicament in FIG. 4D, the vial 14 and injection member 20 is retracted back into the housing 10' by release of the biasing member 15.

FIGS. 5A-F show a cross-sectional container embodiment 500 wherein a gap 45 is provided between the plunger 18 and the plunger rod 23. During use, as a force is exerted on the plunger rod 23, a biasing member 15 is compressed, the vial 14 moves toward the distal end of the housing as shown in FIG. 5C to deliver the injection member 20 from the housing. The flexible tabs 41 remain in contact with the proximal end of the vial 14a, and the gap remains 45 between the plunger 18 and the plunger rod 23. Once the vial 14 has reached the distal end of the housing 10' and the injection member 20 is fully extended, additional force on the plunger rod 23 causes the flexible tabs 41 to move inward as shown in FIG. 5D, and a distal end of the plunger rod 23 to contact the plunger 18 removing the gap there between. Continued force on the plunger rod 23 causes the vial 14 to move toward the distal end of the housing 10' and causes the medicament 16 contained within the vial to be delivered from the device (FIG. 5E). This gap 45 provides, in one embodiment, an additional means of preventing delivery of medicament 16 through the injection member 20 until the injection member 20 is inserted into the target area to a target depth. Following use of the container embodiment 500, the biasing member 15 extends, retracting the vial 14 and the injection member 20 into the housing 10'.

FIGS. 6A-6E include cross sectional sequential views showing the use of the container embodiment 400 shown in FIGS. 4A-E having a housing 10' with a vial 14 including a proximal and distal vial end 14a, 14b, respectively, the vial 14 for housing medicament 16. The container embodiment further including a safety cap 26 housing an injection member cover 30 there within disposed over the distal end of the housing 10', said injection member cover 30 covering the injection member 20. Flexible tabs 41 are shown on the plunger rod 23, and a plunger adaptor component 43 is further provided between tabs 41, as shown in FIGS. 6A-C to account for tolerances in manufacturing in one non-limiting example. The plunger adaptor component 43 can be formed of a deformable material, in some non-limiting embodiments, to account for different spaces and dimensions that may occur during manufacturing. In some non-limiting embodiments, the plunger adaptor component 43 may include a spacer, a bushing, a hat bushing, or any other similar type of component known to those skilled in the art. In another non-limiting embodiment, in some instances, the plunger adaptor component 43 may limit or prevent rotation of the vial 14 or the housing 10' as they moves relative to one another.

While in some non-limiting embodiments provided herein, the at least one resistance feature is shown by flexible tabs on the plunger rod, other possible embodiments of the resistance feature may be provided. The resistance feature of the plunger is configured such that it allows the plunger rod to slide within the vial once the threshold resistance force is met. Other embodiments of this feature may include a telescoping FIG. 7 includes a graphical illustration of the various forces encountered during use of the container embodiments described herein. The graph provides a force (N) on the x-axis versus phase of operation on the y-axis, providing an analysis of insertion force, mechanical fuse force, and break out glide force (BOGF). These are the forces encountered during use of the container embodiments. During a typical injection, a user encounters various forces including an insertion force, followed by a break out glide force. There is typically a rapid transition between these forces. The break out force is the threshold for initial movement and is based on the static friction between the stopper and the vial. The glide force is the resistance force to movement of the plunger and is based on the dynamic friction between the stopper and vial. The insertion force typically ranges from 1-2N (Newtons) and accounts for the force to insert a needle into the skin, the BOGF typically occurs at 5-8N or more, which is the force required to deliver the medicament through the injection member and into the user. If the plunger were to move too soon in the cycle, medicament would be expelled before the needle is at the proper depth. By adding a transitioning step from a mechanical fuse feature that is more precisely controlled that the interference between the rubber stopper and the vial, the device would be more repeatable as to not dispel medicament before the correct needle depth is reached. Consequently, the container embodiments described herein provide a transition between these forces, i.e., a 3-5N mechanical fuse force that is required between the insertion force and the BOGF to control the transition between these two typically encountered forces. The embodiments described herein provide components which interact with one another to govern and smooth this transition, and to ensure that the injection member has been fully inserted into the skin of the user before the medicament is delivered from the container through the injection member.

The one or more plunger adaptors as described herein include components that may be used to account for tolerances in manufacturing. These adaptors provide contact between the flexible tabs and the vial, whether or not the components of the device are made the same size in all devices in manufacturing, in some examples. In some non-limiting embodiments, the one or more plunger adaptors may include a pliable material. The plunger adaptors may control radial dimensions of the container. In other non-limiting embodiments, the plunger adaptor may prevent rotation of the vial as it moves relative to the container. The plunger adaptors can be one or more, and may include a ring like structure or other structure.

In a non-limiting embodiment, the term cap groove, as used herein, includes but is not limited to a groove in the safety cap that interacts with a cap locking tab on the distal portion of the container, or in another, non-limiting embodiment, the groove may be on the distal end of the container, and the cap locking tab may be on the inner surface of the safety cap, such that an interaction between the two would accomplish the task of preventing the cap from being removed from the container after use of the container due to the interaction between the cap locking tab and the cap groove. In one embodiment, the groove may only partially extend into the wall of the safety cap as shown in FIGS. 1A-G, in another non-limiting embodiment, the groove may include an opening which fully extends through the wall of the safety cap, in yet another embodiment the cap groove may include a cut through or recess, or any other type of structure partially or fully extending through the wall of the cap to create resistance between or to provide interaction between the cap locking tab and the cap groove.

Features of the embodiments described herein, including the viewing window, triangular rod with/without visual indicator, e.g. USED indicator, pictorial IFU, rubber contact on plunger rod, or other such features, may be included on any of the embodiments described herein and may be independently combinable, and are not required on any embodiments described herein.

In one embodiment, a method of injecting medicament into a subject is provided. The method includes obtaining a container for delivering a medicament to a target location. The container including a housing having a proximal end and a distal end, the housing including a cap locking tab at the distal end, the container further including a vial having a proximal end and a distal end, the vial configured to contain a medicament, the vial being movable relative to the housing. The container may further include a plunger associated with the proximal end of the vial, the plunger configured to slide within the vial from the proximal end to the distal end of the vial to dispel the medicament from the vial. The plunger may be associated with a plunger rod configured to interact with the plunger. The container may further include an injection member associated with the distal end of the vial, such that medicament dispelled from the vial passes through the injection member to the target location. A slidable interaction member is associated with the distal end of the vial, the slidable interaction member configured to slide with the vial; and a safety cap including a cap groove, the safety cap configured to interact with the distal end of the housing. Moving the vial toward the distal end of the housing causes the slidable interaction member to interact with the cap locking tab, biasing the cap locking tab outward, such that adjoining the safety cap to the distal end of the housing causes the cap groove to interact with the cap locking tab, preventing removal of the safety cap after use of the container.

The method further includes applying the distal end of the container to a target area on the subject and depressing the plunger rod to insert the injection member and deliver the medicament. In a further embodiment, the method may include releasing the plunger rod to allow retraction of the injection member, wherein upon retraction, the injection member is locked within the housing. In still a further embodiment, the method may include removing the safety cap prior to the applying step. In yet a further embodiment, the method may include attaching the safety cap subsequent to the releasing step, whereby the safety cap is permanently locked.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. A container for delivering a medicament to a target location, comprising:
   a housing comprising a proximal end and a distal end, the housing comprising a cap locking tab at the distal end;
   a vial comprising a proximal end and a distal end, the vial configured to contain the medicament, said vial configured to move relative to the housing;
   a plunger slidable within the vial from the proximal end to the distal end of the vial to dispel the medicament from the vial;
   an injection member associated with the distal end of the vial, such that the medicament dispelled from the vial passes through the injection member to the target location;
   a slidable interaction member associated with the distal end of the vial, the slidable interaction member configured to slide with the vial; and a safety cap comprising a cap groove, the safety cap configured to interact with the distal end of the housing;
wherein moving the vial toward the distal end of the housing causes the slidable interaction member to interact with the cap locking tab, biasing the cap locking tab outward, such that adjoining the safety cap to the distal end of the housing causes the cap groove to interact with the cap locking tab, thereby preventing removal of the safety cap after use of the container.

2. The container of claim 1, wherein the safety cap further includes an injection member cover configured to surround the injection member when the safety cap is adjoined to the distal end of the housing.

3. The container of claim 1, wherein a portion of the housing adjacent to the injection member is non-transparent to prevent a user from viewing the injection member during use of the container.

4. The container of claim 1, wherein at least a portion of the housing comprises a viewing window, providing a view into the housing.

5. The container of claim 1 comprising a plunger rod that interacts with the plunger.

6. The container of claim 5, wherein the plunger rod comprises a triangular body comprising a first surface, a second surface and a third surface.

7. The container of claim 6, wherein the proximal end of the plunger and/or the proximal end of the plunger rod further comprises a plunger contact member.

8. The container of claim 7, wherein the plunger contact member comprises a rubber material.

9. The container of claim 6, further comprising a visual indicator on at least one of the first surface, the second surface and the third surface of the plunger rod, wherein the visual indicator provides a status of use of the container to a user of the container.

10. The container of claim 1, further comprising a plunger locking member in the proximal end of the housing, a slidable plunger locking unit associated with the proximal end of the vial, and a plunger lock release member, wherein an interaction between the plunger lock release member and the plunger locking member allows the vial to move relative to the housing to deliver the injection member from the housing.

11. The container of claim 10, wherein sliding the plunger toward the distal end of the vial, and movement of the vial toward the distal end of the housing to deliver the injection member causes the slidable plunger locking unit and the plunger lock release member to move toward the distal end of the housing, releasing the plunger locking member.

12. The container of claim 11, wherein movement of the vial toward the proximal end of the housing, causes the slidable plunger locking unit to move toward the proximal end of the housing, traversing the plunger locking member, such that the plunger locking member biases inward to abut the slidable plunger locking unit preventing movement of the slidable plunger locking unit toward the distal end of the housing.

13. A method of injecting a medicament into a subject, comprising:
obtaining the container of claim 1;
applying a distal end of said container to the target location on the subject; and
depressing a plunger rod that interacts with the plunger to insert the injection member and deliver the medicament.

14. A container for delivering a medicament to a target location, comprising:
a housing comprising a proximal end and a distal end;
a vial comprising a proximal end and a distal end, the vial configured to contain the medicament, said vial configured to move relative to the housing;
a plunger slidable within the vial from the proximal end to the distal end of the vial to deliver the medicament;
a plunger locking member in the proximal end of the housing, the plunger locking member comprising a proximal end and a distal end, wherein the proximal end of the plunger locking member is biased toward a periphery of the housing prior to actuation of the plunger and the proximal end of the plunger locking member is biased toward the plunger following actuation of the plunger; and
a slidable plunger lock release member disposed between the vial and the proximal end of the plunger locking member and associated with a slidable plunger locking unit prior to actuation of the plunger, biasing the plunger locking member toward the periphery, wherein following actuation of the plunger, the slidable plunger locking unit slides toward the distal end of the housing, sliding the plunger lock release member toward the distal end of the housing, such that the proximal end of the plunger locking member is biased toward the plunger, following delivery of the medicament, the vial moves toward the proximal end of the housing, an injection member is retracted within the housing, and the slidable plunger locking unit moves to the proximal end of the housing to abut the proximal end of the plunger locking member preventing a subsequent actuation of the plunger.

15. The container of claim 14, further comprising a slidable interaction member associated with the distal end of the vial, the slidable interaction member configured to slide with the vial.

16. The container of claim 15, comprising a safety cap comprising a cap groove, the safety cap configured to interact with the distal end of the housing, wherein moving the vial toward the distal end of the housing causes the slidable interaction member to interact with a cap locking tab, biasing the cap locking tab outward, such that adjoining the safety cap to the distal end of the housing causes the cap groove to interact with the cap locking tab, thereby preventing removal of the safety cap after use of the container.

17. The container of claim 14, wherein at least a portion of the housing comprises a viewing window, providing a view into the housing.

18. The container of claim 14 comprising a plunger rod that interacts with the plunger.

19. The container of claim 18, wherein the plunger rod comprises a triangular body comprising a first surface, a second surface and a third surface, wherein a visual indicator indicating a status of use of the container is on at least one of the first surface, the second surface and the third surface.

20. A container for delivering a medicament to a target location, comprising:
a housing comprising a proximal end and a distal end, the housing comprising a cap locking tab at the distal end of the housing;
a vial comprising a proximal end and a distal end, the vial configured to contain the medicament, said vial configured to move relative to the housing;

an injection member associated with the distal end of the vial, such that the medicament delivered from the vial passes through the injection member to the target location;

a plunger slidable within the vial from the proximal end to the distal end of the vial to dispel the medicament from the vial;

a biasing member disposed within the housing;

a plunger rod comprising a proximal end and a distal end, wherein application of a force to the plunger rod causes the vial to move toward the distal end of the housing, compressing the biasing member, and delivering the injection member, upon reaching a threshold resistance force wherein at least one resistance feature associated with the plunger rod allows the plunger rod to slide within the vial toward the distal end of the vial to deliver the medicament there within, and following delivery of the medicament, release of the force to the plunger rod causes release of the biasing member, such that the injection member and the vial are retracted into the housing; and wherein the housing further comprises a slidable interaction member associated with the distal end of the vial, the slidable interaction member configured to slide with the vial, and a safety cap comprising a cap groove, the safety cap configured to interact with the distal end of the housing, wherein sliding the plunger toward the distal end of the housing moves the vial toward the distal end of the housing, such that the injection member traverses the target location, further sliding of the plunger toward the distal end of the housing slides the plunger to the distal end of the vial, such that the medicament within the vial is delivered through the injection member, the slidable interaction member interacts with the cap locking tab, biasing the cap locking tab outward, such that adjoining the safety cap to the distal end of the housing causes the cap groove to interact with the cap locking tab, preventing removal of the safety cap after use of the container.

* * * * *